United States Patent

Tjin

[11] Patent Number: 6,166,806
[45] Date of Patent: Dec. 26, 2000

[54] FIBER OPTIC CATHETER FOR ACCURATE FLOW MEASUREMENTS

[76] Inventor: Swee Chuan Tjin, Block 835 Woodlands Street 83, #08-129, Singapore, Singapore

[21] Appl. No.: 09/043,471
[22] PCT Filed: Dec. 14, 1995
[86] PCT No.: PCT/SG95/00012
  § 371 Date: Jan. 28, 1999
  § 102(e) Date: Jan. 28, 1999
[87] PCT Pub. No.: WO97/12210
  PCT Pub. Date: Apr. 3, 1997

[30] Foreign Application Priority Data

Sep. 29, 1995 [SG] Singapore ............................ 9501443-7

[51] Int. Cl.[7] .................................................. G01N 15/02
[52] U.S. Cl. ........................................... 356/336; 385/119
[58] Field of Search ...................... 356/336, 338, 356/342; 600/138, 342, 488, 561; 606/13; 607/88; 385/116, 117, 119

[56] References Cited

U.S. PATENT DOCUMENTS

| | | | |
|---|---|---|---|
| 4,281,929 | 8/1981 | Lord et al. | 385/117 |
| 4,529,267 | 7/1985 | Nishioka et al. | 385/117 |
| 5,512,034 | 4/1996 | Finn et al. | |

*Primary Examiner*—Frank G. Font
*Assistant Examiner*—Tu T. Nguyen
*Attorney, Agent, or Firm*—Pillsbury Madison & Sutro LLP

[57] ABSTRACT

A two-fibre optic probe or sensor performs accurate measurements of fluids flowing within a remote vessels, such as blood flowing within arteries or veins or fluid flowing within pipes. One of the fibre transmits a light that is intercepted by a reflective surface. The reflective surface reflects the light out of the probe through an optically transparent window, located in the probe, and into the volume of the fluid. A portion of the emitted light scatters back, as backscatter, through the optical window into the probe where the light once again encounters the reflective surface. The reflective surface then directs the backscattered light directly into the terminal ends of the other fibre that receives the light. The detected light is used to measure the volume of the fluid at the area where the incident beam of the emitted light and the backscattered light overlaps.

61 Claims, 6 Drawing Sheets

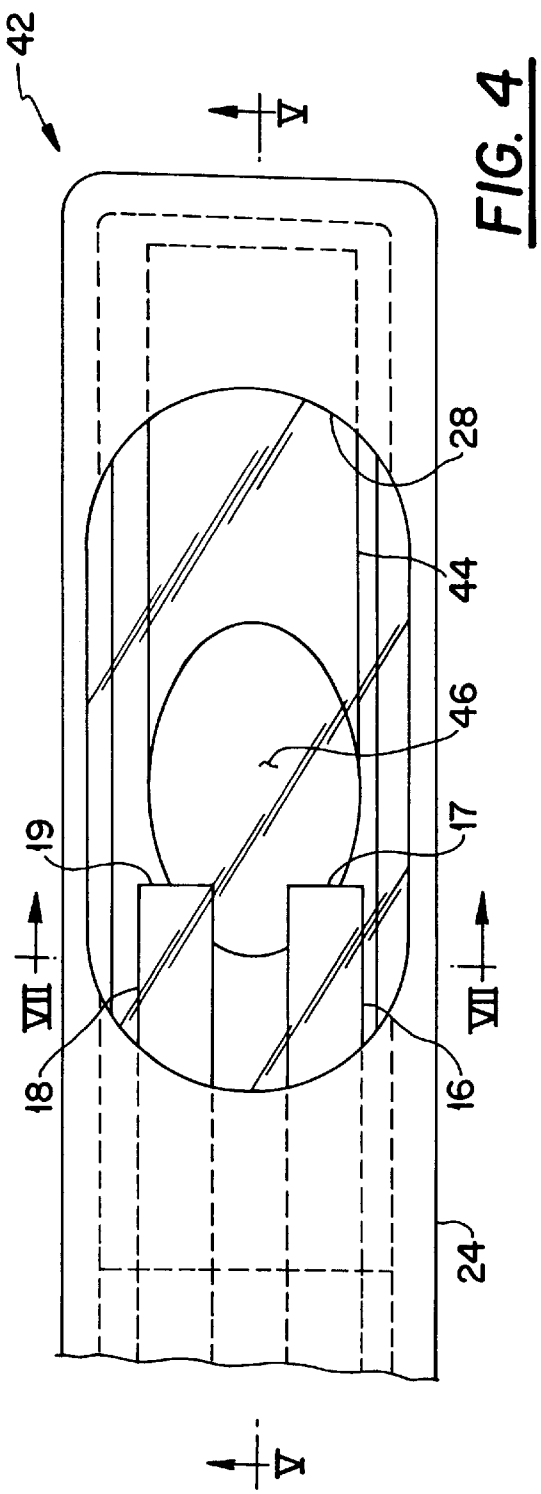
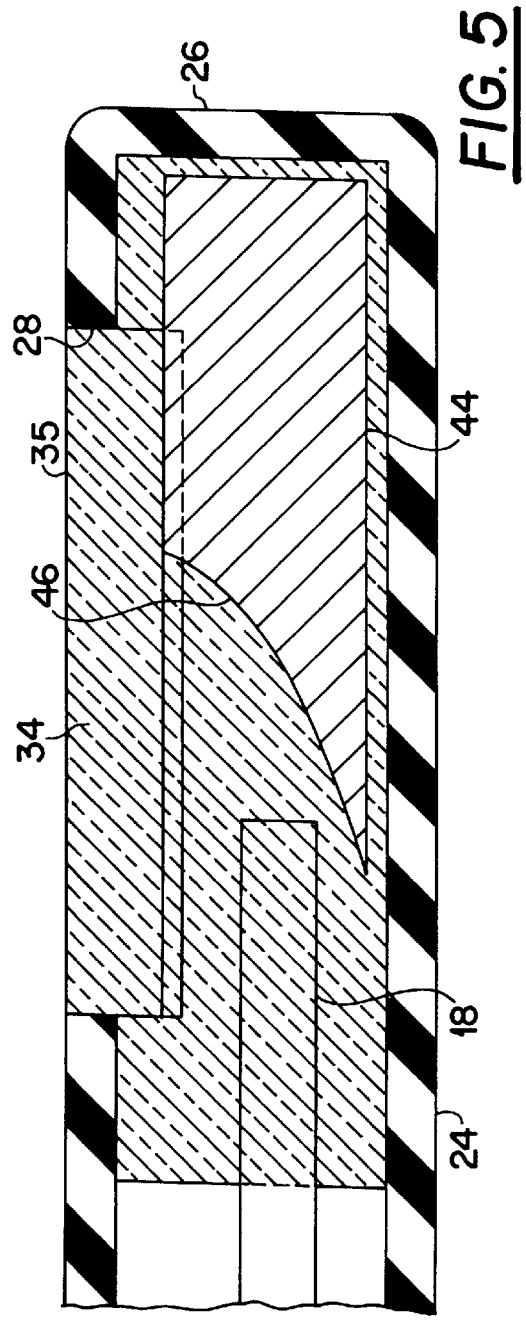

FIBER OPTIC CATHETER FOR ACCURATE FLOW MEASUREMENTS

This application is the national phase of International application PCT/SG95/00012 filed Dec. 14, 1995 which designated the U.S.

BACKGROUND OF THE INVENTION

1. Field of the Invention

The present invention relates to an improved fibre optic probe, or sensor, for remote flow measurements. In particular, this sensor is designed for accurate flow measurements of fluids flowing in remote vessels, such as blood flow within arteries or veins or flows within pipes.

2. Background Information

Fibre-optic anemometry is employed in velocimetry to measure flow rates, velocity gradients, and turbulence at remote points which are otherwise inaccessible. For example, by measuring the velocity of blood flow in an artery before, during, and after an angioplasty procedure, the success of the procedure can be ascertained. Laser light is transmitted, via optic fibres, into the flow where it is scattered. A portion of the scattered light is collected and transmitted, also via optic fibres, to an anemometer for analysis. By analyzing the Doppler shift between the transmitted light and the collected scattered light, the velocity of fluid flow can be ascertained.

Optical fibres were first used in laser Doppler anemometers for the measurement of localized blood flow velocities by T. Tanaka and G. B. Benedek and described in an article entitled Measurement of the Velocity of Blood Flow (In Vivo) Using Fibre Optic Catheter and Optical Mixing Spectroscopy, 14 Applied Optics 189–196 (1975). In their system they used a 500 $\mu$m core diameter monofibre to deliver the laser beam into the femoral vein of a rabbit. The immersed distal end of the fibre was cut and polished at 30° relative to the fibre axis in an attempt to minimize flow disturbance caused by the mere presence of the fibre in the blood stream. A laser beam was projected out through the fibre wall, opposite the cut end surface, into the flow by total internal reflection at the angled polished distal end of the fibre. Light scattered by the erythrocytes at the fibre tip was collected by the same fibre and mixed with the reference beam on the surface of a photomultiplier tube. Analysis of the resultant signal was done on an 18-channel digital autocorrelator.

The sensor of the Tanaka-Benedek system suffers from a number of disadvantages. Projection of light out of the side of the fibre necessitates that the fibre be stripped to its core, thus leaving the brittle and fragile fibre core exposed and unprotected. Cutting and polishing the distal end of the fibre is a difficult operation to perform, thus causing manufacturing complications. Finally, due to the small radius of curvature of the exposed fibre, the curved outer surface of the fibre could cause most of the light scattered back to the fibre to be lost at the fibre-fluid interface, especially if there are irregularities on the surface.

R. B. Dyott, in an article entitled The Fibre-Optic Doppler Anemometer, 2 Microwaves, Optics and Acoustics 13–18 (1978), discusses making flow measurements using a single optic fibre laser Doppler anemometer with the fibre normally terminated. He reported that the region in which light is back-scattered into the fibre extends only to a few tens of the core diameter in front of the fibre tip. As demonstrated in FIG. 10, the flow in this region, indicated at 70, is perturbed by the presence of the distal end of the fibre which could seriously affect the accuracy of any measurements of flow velocity. The Dyott system is well suited, however, to measurements in situations where the medium is stationary and the particles are moving.

For flow measurements, G. A. Holloway, Jr. and D. W. Watkins modified the Tanaka-Benedek system by using separate fibres for delivering the laser beam and receiving the scattered light as described in Laser Doppler Measurement of Cutaneous Blood Flow, 69 J. Investigative Dermatology 306–309 (1977). They applied such a modified system for non-invasive measurement of cutaneous microcirculation. The disadvantages described above regarding the single fibre Tanaka-Benedek system are exacerbated by the inclusion of a second fibre.

For invasive flow measurements, D. Kilpatrick adapted Dyott's system by modifying the analyzing components and described the adapted system in Laser Fibre Optic Doppler Anemometry in the Measurement of Blood Velocities In Vivo, Computers in Cardiology, IEEE, 467–470 (1980). By using this system, he showed that, despite flow perturbation caused by the presence of the fibre, the system could still be used to measure blood flow velocities both in vitro and in vivo. With the fibre positioned parallel to fluid flow he obtained a broad spectrum, declining monotonically with width, that is proportional to the flow velocity. The maximum Doppler shift frequency was taken as representative of the flow velocity and this agreed with the calculated theoretical value of 4.2 Mhz/ms$^{-1}$ (i.e. the maximum shift frequency is absolutely calibrated). A linear relationship was obtained between the maximum shift frequencies and the flow velocities for flows of up to 1.5 ms$^{-1}$ in the forward direction (advancing towards the fibre tip) but only 20 cms$^{-1}$ for flows in the reverse direction (moving away from the fibre distal end tip).

Concurrently with the work of Kilpatrick described above, M. Imamura, F. Kajiya, and N. Hoki independently developed a similar system, but with an added advantage of being able to measure directional flow, as reported in Blood Velocity Measurement By Laser Doppler Velocimetry With Optical Fibre, Proc. 12th Int. Conf. Med. and Biol. Eng. 35 (1979). They achieved this by using a Bragg cell (acousto-optic modulator) to shift the reference signal by 40 MHz. In vivo flow measurements in blood were made via the fibre's distal end and with the whole fibre oriented at a 60° angle to the flow (see FIG. 11), and a broad rectangular spectrum was obtained. A linear relationship was again found between the maximum shift frequencies and flow velocities as in the Kilpatrick adaptation of the Dyott system.

It is interesting to note the absolutely calibrated linear relationship between the maximum Doppler shift frequency and flow velocity obtained for the Kilpatrick and Imamura-Kajiya-Hoki systems described above. This relationship implies that single fibre systems measure the free stream flow velocity (i.e, velocity outside the perturbed region), but only within certain velocity limits. Outside these limits, however, the system will either have to be modified or improved to allow an accurate measurement of flow velocity. The broad spectrum observed by both systems was assumed to be due to multiple frequency shifts from the particles of varying velocity in the perturbed region at the tip of the fibre.

The slight difference in spectral shape reported by the Kilpatrick and the Imamura-Kajiya-Hoki studies is due to the area of turbulence at the measurement region adjacent the fibres' distal end, and this has been theoretically addressed by M. D. Stern in Laser Doppler Velocimetry in Blood and Multiply Scattering Fluids: Theory, 24 Applied Optics 1968–1986 (1985). The difference was attributed to different thicknesses of the boundary layer at the distal end tip of the fibre, with Kilpatrick's system having a thicker layer. To overcome the effect of the boundary layer for obtaining accurate flow measurements, it is necessary to project the probe volume (i.e., the volume in which flow measurements are made) away from or beyond the boundary layer and into the laminar flow region. To do this Stern suggested use of two fibres, with one fibre delivering the incident light and the other collecting the scattered light. The sensor proposed by Stern, however, projected the probe volume from the blunt ends of the fibres.

A two fibre laser Doppler anemometer with the fibres oriented at 60° to the direction of flow was developed, tested, and reported by Y. Ogasawara, O. Hiramatsu, K. Mito, and others in A New Laser Doppler Velocimeter With a Dual Fibre Pickup For Disturbed Flow Velocity Measurement, Circulation, 76, Suppl. 4, 328 (1987) and by F. Kajiya, O. Hiramatsu, Y. Ogasawara, and others in Dual-Fibre Laser Doppler Velocimeter and its Application to the Measurements of Coronary Blood Velocity, 25 Biorheology 227–235 (1988). In both systems, two step-index fibres with a core diameter of 50 μm and a cladding diameter of 62.5 μm were used. The scattered light collected by the receiving fibre was mixed with the reference beam and detected using an avalanche photodiode. The spectrum analyzer showed a narrow spectrum (as compared with the single fibre system) with a peak value that varied with flow velocity. The separation between the cores of the two fibres in these systems was 12.5 μm.

By varying the core separation and using different fibre combinations, S. C. Tjin, D. Kilpatrick, O. Hiramatsu, Y. Ogasawara, and F. A. Kajiya obtained better linearity between the Doppler frequencies and flow velocities as the core separation was increased with their system and findings described in A Dual-Fibre Laser Doppler Anemometer for in Vitro Measurements, Proc. 13th Aust. Conf. Optical Fibre Technology, 245–248 (1988). This improved linearity, however, was obtained at the expense of a decreased signal-to-noise ratio, and the probe volume was still projected from the distal end of the fibre.

However, with a fibre probe placed parallel to the flow, S. C. Tjin, D. Kilpatrick, and P. R. Johnston found that a two-fibre probe with the fibre tips normally terminated is inadequate for accurate flow measurements, especially for flows moving away from the fibre tips, as described in Evaluation of the Two-Fibre Laser Doppler Anemometer for In Vivo Blood Flow Measurements, Experimental and Flow Simulation Results, 34 Optical Engineering, 460–469 (1995). This is because the flow at the fibre distal end tips is perturbed, and the region of perturbation extends away from the fibre tips with increasing flow velocity. For flow towards the fibre tips, the region of flow perturbation decreases towards the fibre tips with increasing flow velocity. These changes in the region of flow perturbation with flow velocities and the direction of flow give rise to a non-linear calibration between the Doppler frequency and the flow velocity. This limits the usefulness of the system for in vivo flow measurements because, in most practical systems, the fibre optic probe must be placed parallel to the flow.

A two fibre sensor adapted to project a probe volume to the side of the catheter wall by means of reflective surfaces was proposed by S. C. Tjin in Fibre Optic Laser Doppler Anemometry, Ph.D. Thesis, University of Tasmania, 1991, available at the University of Tasmania. Such a sensor was, however, never constructed. In the proposed embodiment of the sensor, two fibres are embedded in the wall of a larger catheter. Proximate each fibre distal end tip, a separate opening is formed in the catheter sidewall. An angled reflective surface is positioned in the opening axially opposite the fibre distal end tip to reflect light from the fibre radially outwardly through the opening directly into the flow, which is parallel to the fibre axes. This proposed embodiment, if built, would have had a number of disadvantages. The uncovered openings at the reflective surfaces would themselves cause turbulence and would also provide a place for blood clots to form or collect. To minimize the size of the openings, and thus the amount of turbulence caused thereby, it was proposed that two small, circumferentially spaced apart openings be provided in the catheter wall rather than a single large opening and single reflective surface that would be able to accommodate both fibres. Polishing, mounting, and aligning dual reflective surfaces, however, would introduce manufacturing complexity and alignment problems to developing a suitable probe volume and would add cost to the manufacture of the sensor. Also, the embodiment, as proposed, included no provision for focusing the transmitted and received light beams to minimize the width of the Doppler spectrum and maximize the signal-to-noise ratio.

SUMMARY OF THE INVENTION

An object of the present invention is to provide a two-fibre probe that avoids the problem of non-linear calibration between the Doppler frequency and the flow velocity due to flow perturbation caused by the sensor. In addition, an object of the present invention is to provide a sensor that projects a probe volume to the side of the sensor to avoid turbulence caused by the sensor, the sensor being relatively simple to manufacture and eliminating structural features that would themselves cause turbulence or collect blood clots.

Consistent with this object, a new two fibre optic measuring probe has been designed, which can be incorporated into any existing catheter, to provide accurate fluid flow measurements, not axially via the distal end of the fibre, but radially with respect to the axes of the fibres. The measuring probe comprises two or more optical fibres placed alongside each other within a flexible tube. Light is transmitted into the blood stream through one of the fibres, termed the transmitting fibre. A reflective surface, located axially within the flexible tube relative to the terminal ends of the fibres, is polished or otherwise formed with the reflective surface oriented at an angle with respect to the axes of the fibres. The reflective angled surface will reflect the light from the transmitting fibre, through an optically transparent window in the sidewall of the tube. Thus, light is reflected into the blood stream alongside the catheter where blood flow is not usually perturbed by the presence of the catheter and is more likely to be laminar.

This radially projected light is scattered by scattering particles within the probe volume, thus developing back-scatter light with part of the backscatter light being collected by the other fibre, termed the receiving fibre.

A cavity surrounding the ends of the optical fibres and the reflective surface is filled with an appropriate optical cement to both fix the optical fibres and the reflective surface in place and to provide an optical window for the sensor that is flush with the outer surface of the catheter tube. This minimizes flow perturbations along the side of the sensor and also prevents blood from entering a cavity where it may contribute to the formation of undesirable clots.

Variations on this design include a variety of shapes for the fibre tips, including tips that are normal to the fibre axes or tips that are concave or convex. Concave and convex fibre tips serve the additional purpose of being able to effectively focus the incident and received beams at more specific locations to increase the intensity of the incident beam and to narrow the field of view of the receiving beam to effectively shrink the size of the probe volume and thus improve the signal to noise ratio and the Doppler spectrum Another variation of the measuring probe of the present invention includes a reflective surface that is concave instead of flat. This concave surface also helps focus the beam from the transmission fibre to a point above the surface of the optical cement surface. Part of the light scattered by scattering particles in this region is collected by the receiving fibre via the concave reflecting surface. A concave reflective surface can be combined with fibres having concave or convex tips.

Other objects, features and characteristics of the present invention will become apparent upon consideration of the following description with reference to the accompanying drawings, and in the appended claims, all of which form a part of the specification, and wherein reference numerals designate corresponding components of the figures.

BRIEF DESCRIPTION OF THE DRAWINGS

FIG. 4 is an enlarged view of a second embodiment of the sensor tip according to the present invention from above the reflective surface;

FIG. 5 is a cross-sectional view of the second embodiment of the sensor tip of the present invention along the line V—V in FIG. 4;

DETAILED DESCRIPTION OF THE INVENTION

Figure 1:
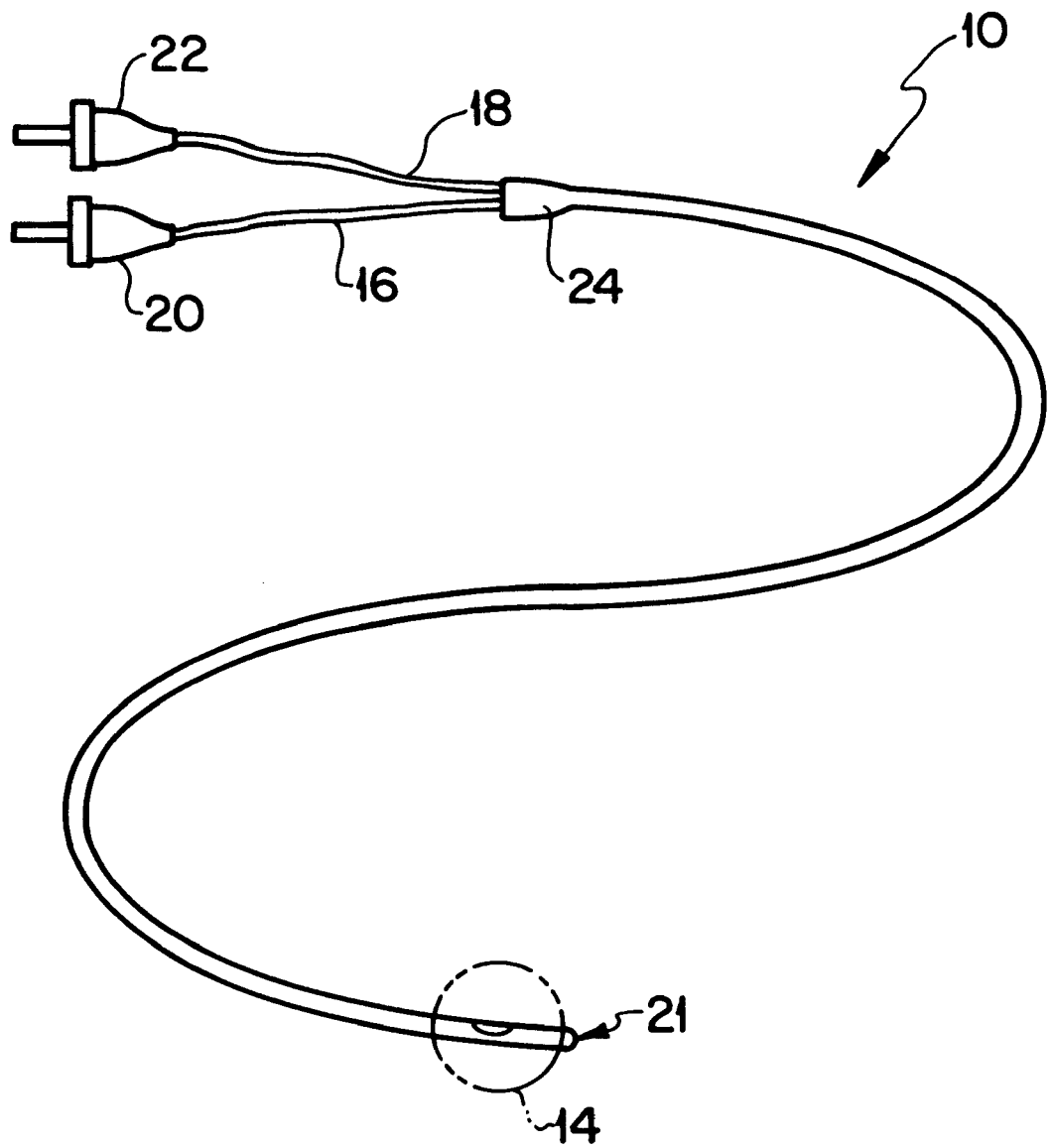
FIG. 1 shows a conventional catheter incorporating an improved measuring probe, or sensor tip, according to the present invention.

A fibre optic catheter 10 having a measuring sensor 14 according to the present invention is shown in FIG. 1. The catheter 10 includes first and second optic fibres 16, 18 enclosed within a flexible tube 24. The fibres are conventional optical fibres and can, for example, be comprised of glass or plastic. Glass fibres are preferred because of their superior light transmission qualities. The flexible tube is preferably a medical grade tubing, such as heparin (an anticoagulant) coated latex, which is conventionally used in a variety of in vivo applications.

A sensor tip, or region, 14 is located adjacent, but proximally of, a distal end of the catheter 10, or at any desired location therealong. Conventional connectors 20, 22 are fixed to the proximal ends of the optic fibres 16, 18, respectively. The connectors 20, 22 connect the catheter 10 to an anemometer or other suitable analyzing device. With the exception of the use of the present invention sensor, the catheter 10, including the connectors 20, 22, is of conventional construction and design for a two optic fibre catheter.

Figure 2:
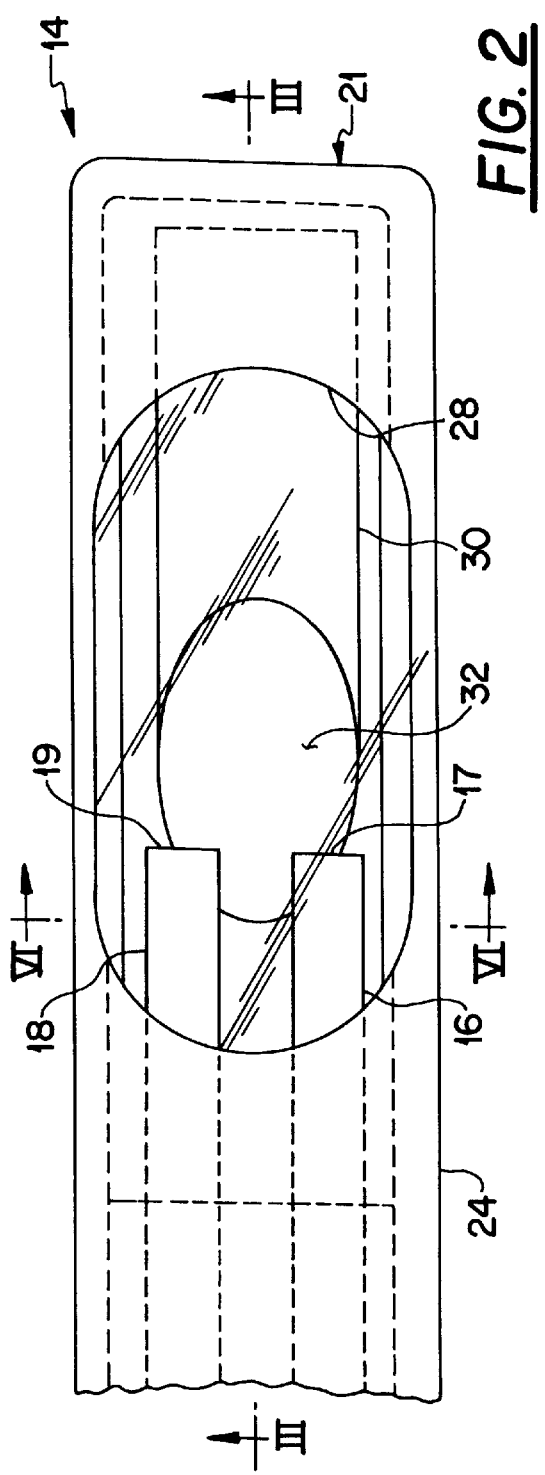
FIG. 2 is an enlarged view of the sensor tip of the present invention from above the reflective surface.
Figure 3:
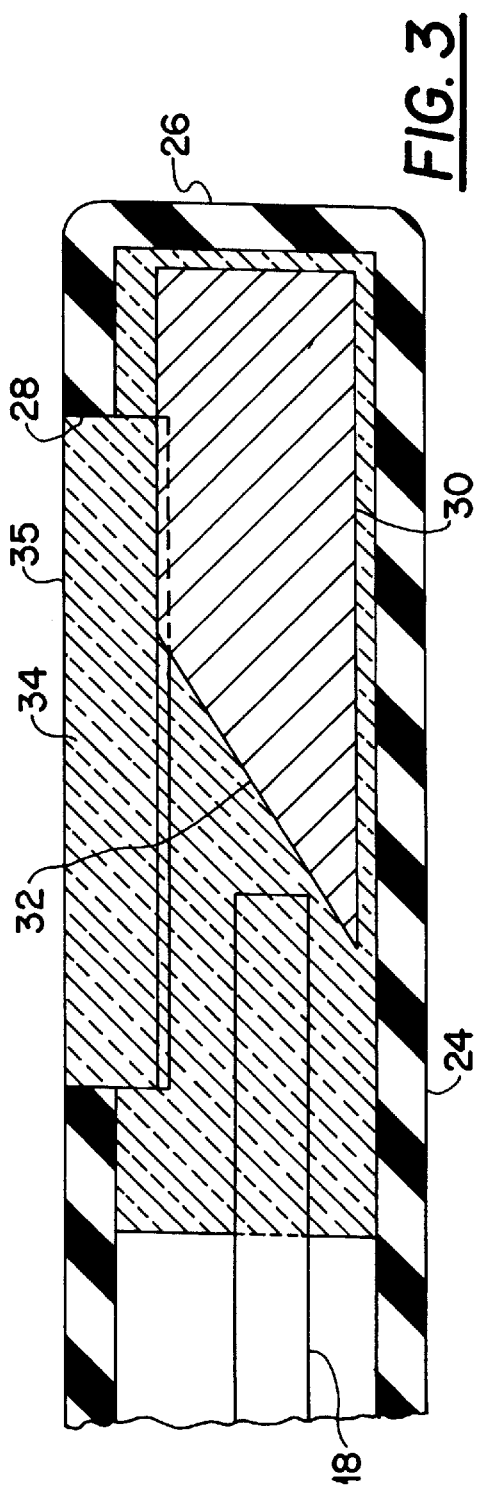
FIG. 3 is a cross-sectional view of the sensor tip of the present invention along the line III—III in FIG. 2.

The construction of the sensor in the sensoring region 14 is shown in more detail in FIGS. 2 and 3. The optic fibres 16, 18 are enclosed by the flexible tube 24 and may terminate within the tube 24 near, but spaced proximally from, the distal end 21 of the catheter. It is presently preferred to use multimode fibres having a step refractive index profile with a core diameter of 50 $\mu$m and a cladding diameter of 125 $\mu$m (denoted a 50/125 fibre). A single mode fibre, having a core diameter of 8 $\mu$m and a cladding diameter of 125 $\mu$m (a 8/125 fibre), may also be used. It is also possible to use a combination of one single mode fibre and one multimode fibre. For single mode fibres, the preferred core diameter is dependent on the wavelength of light to be used.

The distal end 21 of tube 24 is preferably closed by a cap 26, or the like, to prevent the intrusion of blood into the probe which might form undesirable clots.

An opening 28 is initially formed in a sidewall of the tube 24. The terminal ends 17, 19 of the optic fibres 16, 18, respectively, are located within the tube 24 adjacent opening 28.

A plug 30 composed of reflective material is disposed within the tube 24 between the terminal ends 17, 19 of the optic fibres 16, 18 and the distal end cap 26 of the tube 24. The plug 30 may be composed of any suitable reflective material, such as copper, stainless steel, silver, mirrored glass, or the like. Presently a portion of stainless steel wire having a diameter of 0.2 mm has been employed.

One end of the plug 30 nearest the terminal ends 17, 19 is ground and polished to form a finished reflective surface 32 that is oriented at an angle with respect to the longitudinal fibre axes of the fibres 16, 18. It is presently contemplated that the preferred angle of the reflective surface be within the range of about 25–35° with respect to the longitudinal fibre axes of the fibres 16, 18, with an angle of about 30° being preferred.

Once the fibres and the reflective surface are appropriately aligned, the cavity within the opening 28 surrounding the optic fibres 16, 18 and the plug 30 is filled with an optical cement 34. The optical cement may include any suitable optically transparent material having an initial liquid phase and which hardens after being poured into the cavity, such as clear polymeric materials which harden upon exposure to certain radiation. When set, the optical cement 34 locks the fibres and the reflective surface 32 together into an integral unit. The cement 34 also provides a smooth surface over the opening that is flush with the outer peripheral surface of tube 24. To this end, it is necessary that the optical cement, forming an optical window 35 when finished, be polished smooth to minimize turbulence caused by the surface and to prevent blood clots from forming in voids and other irregularities in the cement. The preferred optical cement is Norland™ Optical Adhesive 61. It should be understood, however, that other optical quality cements can also be employed.

In operation, with the catheter inserted into the blood vessel of a patient or into a flow within a pipe, a transmission, or incident, beam of light from a laser, such as, preferably, a laser diode, such as, for example, the 7350 Series Diffraction Limited Laser Diode, operating in the wavelength range of 670–680 nm, produced by SDL, Incorporated of San Jose, Calif., U.S.A., or an HeNe laser, exits the terminal end 17 of the optical fibre 16, here designated as the transmitting, or transmission, fibre. The wavelength of the light may be any wavelength within the scattering spectrum of blood, which ranges from 450–850 nm. Wavelengths within the red portion of the spectrum, 600–720 nm, are preferred because they provide the most scattering within blood.

Figure 6:
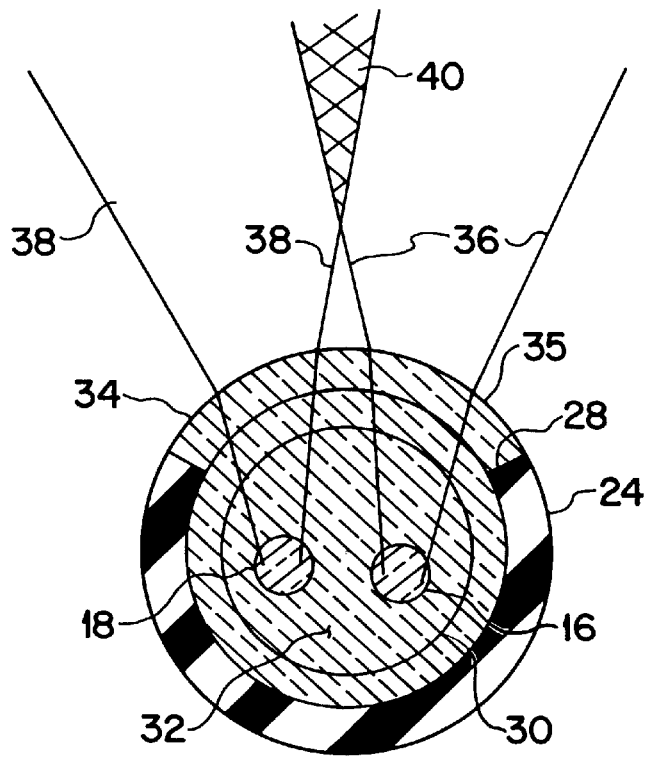
FIG. 6 is a cross-sectional view of the of the sensor tip of the present invention along the line VI—VI in FIG. 2.

The incident beam reflects off the reflecting surface 32 in a direction having a component normal to the fibre axes out of the optical window 35 formed over the opening 28 in the tube 24 (see FIG. 6). The light within the incident beam is reflected into a measurement, or probe, volume of fluid flow outside of and alongside the tube 24 in the region near the optical window 35. The reflected light is scattered by particles flowing within the measurement volume. A portion of the light is also scattered back (the backscatter) through the optical window 35 where it is reflected by the reflecting surface 32 into the terminal end 19 of the optical fibre 18, here designated as the receiving fibre. The light received by the receiving fibre 18 is known as the backscatter signal.

As shown in FIG. 6, the reflected light emitted from the transmitting fibre 16 covers a diverging area denoted between lines 36, that can be considered as a transmitted acceptance cone. The receiving fibre 18 collects light from a diverging area, or acceptance cone or field of view, denoted between lines 38. The overlap of the transmitted acceptance cone 36 with the field of view 38, as shown by the cross-hatched area 40, represents the probe volume region wherein the incident beam and the backscatter transmission overlap. It is in this probe volume where fluid flow is measured.

The design parameters and the preferred values of those parameters will now be described.

Depending on the angle of the reflective surface, the probe volume may be projected out of the optical opening normal to the fluid flow (i.e., normal to the fibre axes) or forwardly or rearwardly with respect to the fibre tips. To obtain the largest Doppler shift, however, it is preferred that the probe volume be projected as far forwardly or rearwardly as possible. If the probe volume is projected normally to the fibre axes, there is no Doppler shift and the flow velocity cannot be ascertained.

In addition, the height of the probe volume above the wall of the catheter 24 (i.e., the distance the probe volume 40 in FIG. 6 is spaced radially from the optic window 35 ) is also critical. The probe volume must be a sufficient distance, or at a sufficient projection height, from the catheter so that the probe volume is out of the boundary layer of the flow along the sidewall of catheter 24. On the other hand, if the probe volume is too far from the catheter sidewall, the laser transmission light cannot sufficiently penetrate the opaque fluid, such as blood. The projection height of the probe volume, thus, depends on a number of factors, including the index of refraction of the optical cement and the angle of the reflective surface. The greater the reflective surface angle, the higher the projection height. Projection height also depends on the position of the reflective surface with respect to the fibre tips. The closer the reflective surface is to the fibre tips, the higher the projection height. Finally, the projection height depends on the separation between the two fibres. The greater the separation, the greater the projection height.

To ensure that the acceptance cones of the transmission fibre and the receiving fibre are correctly projected out of the catheter and window 35, the two cones should intersect beyond the reflective surface. In other words, the two cones, between lines 36 and 38, respectively, cannot overlap until they are projected into the flow as shown in FIG. 6. To avoid overlap of the acceptance cones prior to their exiting optical window 35, the fibre core centers must be spaced at least 260 $\mu$m apart.

In addition, the reflective surface cannot be too far from the fibre tips. The beam angle of the transmission light depends on the index of refraction of the optical cement. Using the preferred optical cement, Norland™ Optical Adhesive 61, which has an index of refraction of 1.5562, the acceptance cones of two 50/125 multimode fibres, whose cores as separated by 260 $\mu$m, will intersect each other at a distance of 290 $\mu$m from the fibre tips. Therefore, the intersection of the fibre axes with the reflective surface must be within 290 $\mu$m of the fibre tips.

Although it is preferred that the probe volume 40 be projected as far forwardly or rearwardly along the catheter 24 as possible, the angle of the reflective surface cannot be so great or so small that the reflected transmission light does not leave the optical window due to total internal reflection. To avoid total internal reflection, the angle of the reflective surface must be between 25–65° from the fibre axes, but not, preferably, exactly at 45°. Where the angle is progressing greater than 45°, the probe volume will be progressively projected rearwardly; as the angle becomes less than 45°, the probe volume will be progressively projected forwardly. At a 45° reflective angle, the probe volume is projected normal to the fibre axes.

A forwardly projected probe volume is preferred. A normally projected probe volume would not capture sufficient Doppler shift, as noted above. While a rearwardly projected probe volume may be blocked by the fibres themselves, this could be avoided by moving the fibres away from the reflective surface. This can, however, result in the acceptance cones of the fibres overlapping before reaching the reflective surface.

As noted previously, the angle of the reflective surface is preferably within the range of 25–35°, with 30° being preferred. If the angle is less than 25° total internal reflection will result. If the angle is greater than 35° the projection height will be too high.

The optical opening must be large enough so that the acceptance cones of the fibres are not blocked by the tube wall. For a sensor having 50/125 multimode fibres with a 260 $\mu$m separation between the fibre axes, an optical cement having an index of refraction of 1.5562, and a reflective surface with an angle of 30°, the optical opening must have an axial length of at least 600 82 m measured axially from the fibre tips 17, 19 and a circumferential width of at least 530 $\mu$m that is centered between the optical fibres.

The plug 30 must have a sufficient diameter such that the acceptance cones of the fibres are entirely captured by the reflective surface. The diameter of the catheter primarily preferred herein is 1.2 mm. For a 1.2 mm diameter sensor having 50/125 multimode fibres with 135 $\mu$m separation therebetween, an optical cement having an index of refraction of 1.5562, a reflective surface at an angle of 30°, and with the fibre axes intersecting the reflective surface at a distance of 108.25 $\mu$m from the fibre tips, the outer diameter of the plug must be at least 204 $\mu$m.

For a sensor employing two 8/125 single mode fibres, the design parameters are summarized below:

| | |
|---|---|
| Refractive index of optical cement | 1.5562 |
| Recommended reflective angle | 27° |
| Minimum plug diameter | 150 μm |
| Minimum optical opening length for a 1.2 mm diameter sensor. | 400 μm |

It must be noted that the above preferred parameters have been developed for prototype sensors having flat reflective surfaces and normally positioned fibre tips. Any or all of the parameter values may differ in a preferred commercial embodiment from those cited above. In addition, it is important to understand that all of the parameters are directly interdependent and that variation of any one of the preferred values would necessarily change the remaining values.

In manufacturing the sensor of the present invention, the fibres are inserted into the tube with the plug on which the reflective surface is polished. Incident light transmitted through the transmission fibre and a received light signal are both monitored. The relative orientation of the fibres with respect to the protective surface is adjusted until the signal to noise ratio is maximized. The optical cement is then added to fix the relative positions of the fibres and the reflective surface.

The sensor of the present invention has been described thus far as having a single optical opening and window and a single reflective surface whereby the single window and reflective surface are associated with both fibres and each, respectively, transmits and reflects both the incidence signal and the backscatter signal. The sensor of the present invention could, however, include two or more reflective surfaces axially disposed with respect to associated fibre tips in a corresponding number of optical openings having associated optical windows. In this embodiment, it is contemplated that the incidence beam, emitted from a transmitting fibre, is reflected by its associated reflective surface out its associated optical window. Similarly, the backscatter signal passes through an optical window and is reflected by a reflective surface associated with a receiving fibre.

The sensor of the present invention has also be described as having a single transmitting fibre and a single receiving fibre. It is presently contemplated, however, that the sensor of the present invention could include two or more transmitting fibres and/or two or more receiving fibres, at least one optic transmitting path and at least one optic receiving path being required.

It is desirable that the Doppler spectrum be as narrow as possible and that the signal to noise ratio be as large as possible. To maximize the signal to noise ratio from the sensor, and to minimize the width of the Doppler spectrum, it is desirable that the probe volume be as small as possible and that the transmission beam be as concentrated as possible. To that end, a sensor with the capability to focus the transmission signal and to focus the field of view of the receiving fibre would provide significant advantages over sensors without such capabilities.

Figure 7:
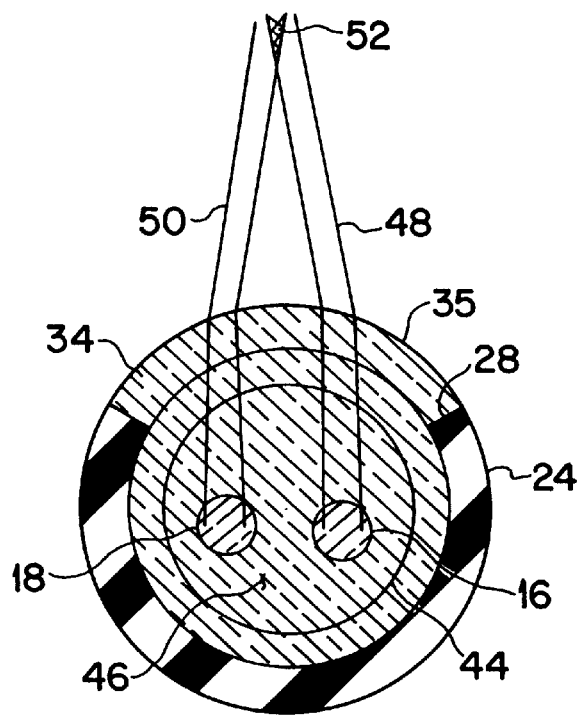
FIG. 7 is a cross-sectional view of the sensor tip of the present invention along the line VII—VII in FIG. 4.

An alternate embodiment of the fibre optic catheter of the present invention, which includes such focusing capability, is shown in FIGS. 4, 5, and 7. The sensor tip 42 of the catheter of the alternate embodiment is, in most respects, identical to the sensor tip 14 of the first embodiment. The reflective surface 46 of the plug 44 is not, however, ground flat as in the first embodiment, but is ground with a concave shape as shown schematically in FIG. 5. As demonstrated in FIG. 7, the concave surface helps focus the incident beam 48 from the transmission fibre 16 to a smaller region above the surface of the sensor. Furthermore, by virtue of the concave reflective surface 46, the region from which light is collected by the receiving fibre 18, indicated between lines 50, is also focused so as to be narrower than without such focusing. This results in a narrower probe volume 52 which causes a stronger signal to noise ratio and a narrower Doppler spectrum.

As noted above the index of refraction of the optical cement presently used is 1.5562. The index of refraction of the fibre core typically ranges from about 1.4–1.5. Accordingly, the acceptance cone of the transmission beam is enlarged upon being emitted from the fibre tip into the optical cement. This results in an undesired enlargement of the probe volume and a decrease in the light intensity. If the index of refraction of the optical cement were less than that index of refraction of the fibre core, however, the acceptance cone would shrink, resulting in built-in focusing effect.

As noted above, the shape of the reflective surface can itself be modified to focus the transmission signal and the field of view of the receiving fibre. Similarly, the tips of the fibres may be shaped so as to produce such a focusing effect.

Figure 8A:
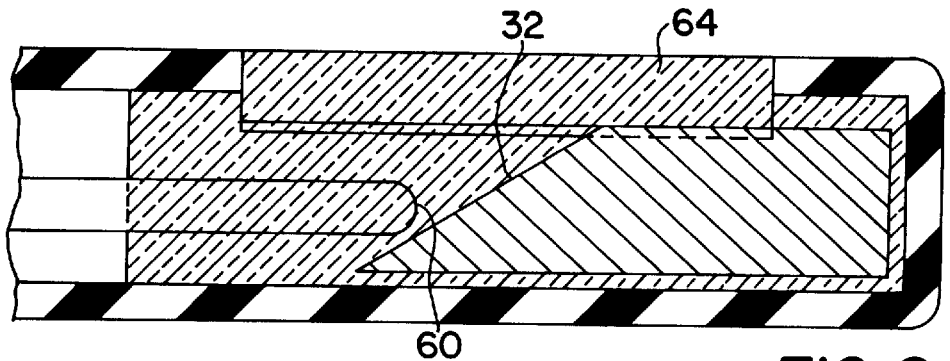
FIG. 8A is a cross sectional view of the sensor of the present invention depicting a third embodiment thereof.
Figure 8B:
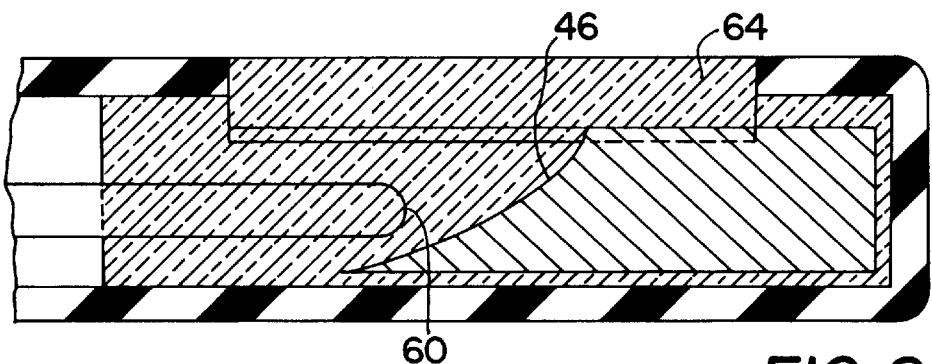
FIG. 8B is a cross sectional view of the sensor of the present invention depicting a fourth embodiment thereof.

Further embodiments of the sensor of the present invention are shown in FIGS. 8 and 9. The sensor of FIG. 8A, has fibre tips 60 that are convex in shape. Where the index of refraction of the optical cement 64 is less than the index of refraction of the fibre core, the convex fibre tips 60 of the sensor of FIG. 8A will result in a more focused probe volume and thus a stronger signal to noise ratio and narrower Doppler spectrum. Conversely, where the index of refraction of the optical cement 64 is greater than the index of refraction of the fibre core, the convex fibre tips 60 of the sensor of FIG. 8A will result in a less focused probe volume.

The sensor of FIG. 8A has a flat reflective surface 32. The sensor of FIG. 8B, has fibre tips 60 that are convex combined with a concave reflective surface 46 resulting in even more focusing of the probe volume.

Figure 9A:
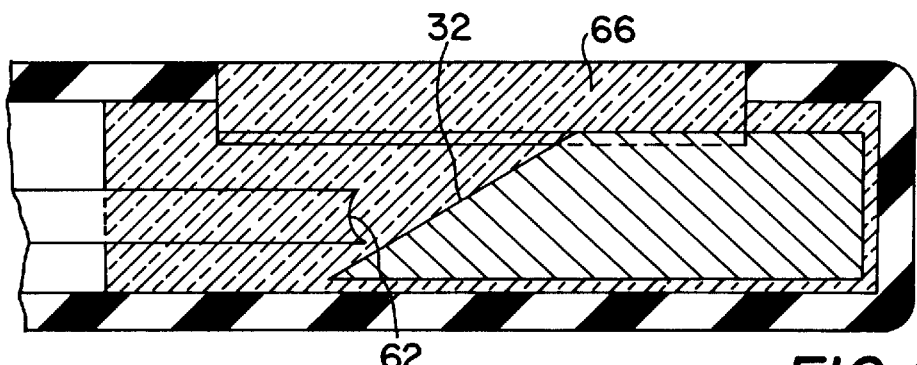
FIG. 9A is a cross sectional view of the sensor of the present invention depicting a fifth embodiment thereof.
Figure 9B:
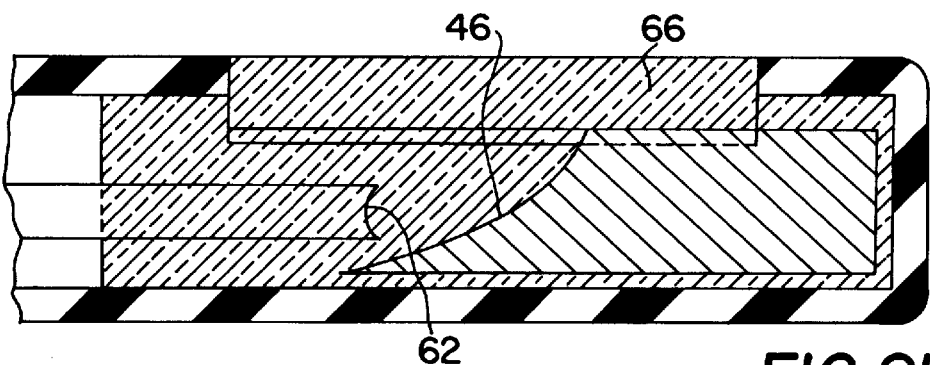
FIG. 9B is a cross sectional view of the sensor of the present invention depicting a sixth embodiment thereof.
Figure 10:
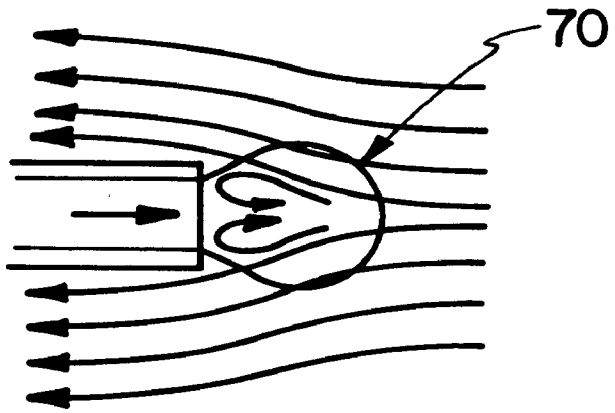
FIG. 10 shows flow perturbation occurring at the blunt end of a prior art sensor tip.
Figure 11:
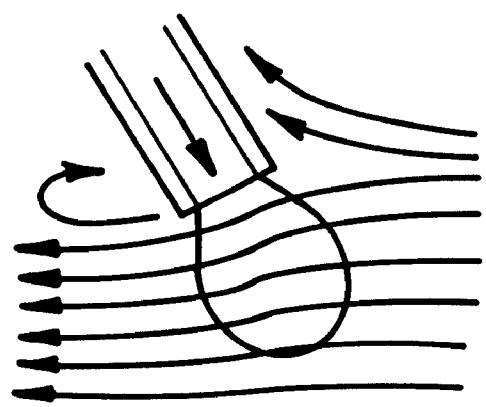
FIG. 11 shows the flow perturbation occurring at the end of a prior art sensor tip oriented at 60° to the flow.

The sensor of FIG. 9A, has fibre tips 62 that are concave. Where the index of refraction of the optical cement 66 is greater than the index of refraction of the fibre core, the concave fibre tips 62 of sensor of FIG. 9A will result in a more focused probe volume and thus a stronger signal to noise ratio and narrower Doppler spectrum. Conversely, where the index of refraction of the optical cement 66 is less than the index of refraction of the fibre core, the concave fibre tips 62 of sensor of FIG. 9A will result in a less focused probe volume.

The sensor of FIG. 9A has a flat reflective surface 32. The sensor of FIG. 9B, has fibre tips 62 that are concave combined with a concave reflective surface 46 resulting in even more focusing of the probe volume.

In analyzing the signals received by the receiving fibre of the two-fibre sensor, the backscatter signal is compared to the incident signal in a known manner so as to determine the Doppler shift of the backscatter signal. As is well known in the art, the flow velocity of fluid, such as blood, is directly proportional to Doppler shift frequency. The velocity may be represented mathematically by the expression:

$$V = K \cdot f_D$$

where,
V=Blood Flow Velocity;
K=Doppler shift constant to be determined in a known manner; and $f_D$=the Doppler shift frequency, to also be determined in a known manner.

The Doppler shift constant K is calculated by the following equation:

$$K = -\frac{2n}{\lambda}\cos\theta$$

where, n=index of refraction of blood=1.33;

θ=obtuse angle between direction of flow and the bisection of the transmission cone projected from the optical window; and λ=wavelength of the light.

While the invention has been described in connection with what are presently considered to be the most practical and preferred embodiments, it is to be understood that the invention is not to be limited to the disclosed embodiments, but, on the contrary, it is intended to cover various modifications and equivalent arrangements included within the spirit and scope of the appended claims.

Such modifications, which would be included within the scope of the appended claims, include, but are not limited to, a fibre optic sensor having two or more transmitting fibres and/or two or more receiving fibres and a sensor having two or more reflective surfaces axially disposed with respect to associated fibre tips in a corresponding number of optical openings having associated optical windows.

Thus, it is to be understood that variations in the particular parameters used in defining the improved fibre optic probe can be made without departing from the novel aspects of this invention as defined in the claims.

What is claimed is:

1. A sensor for remote fluid flow measurements, said sensor comprising:
    a flexible tube having an optical opening formed in a sidewall thereof;
    first and second optical fibres disposed within said tube, said first and second optical fibres each having a longitudinal fibre axis and a terminal end disposed within said tube proximate said optical opening; and
    a single reflective surface disposed within said tube adjacent said terminal ends of said first and second optical fibres, said single reflective surface being separate from said terminal ends,
        wherein said optical opening and a portion of said tube surrounding said terminal ends of said first and second optical fibres and said reflective surface define a cavity, said cavity being filled with an optical cement forming an optical window,
        said single reflective surface being oriented such that light emitted from said terminal end of one of said first and second optical fibres is reflected by said single reflective surface in a direction having a component normal to the fibre axes through said optical cement into a measurement volume of the flow located outside and alongside said sensor, the reflected light being scattered within the measurement volume such that a portion of the scattered light that is within a field of view of the other of said first and second optical fibres is scattered back through said optical cement and is reflected by said single reflective surface into said terminal end of the other of said first and second optical fibres.

2. The sensor of claim 1 wherein said single reflective surface is flat.

3. The sensor of claim 1 wherein said single reflective surface is concave.

4. The sensor of claim 1 wherein said single reflective surface is disposed adjacent the distal end of said tube.

5. The sensor of claim 1 wherein said single reflective surface is composed of stainless steel.

6. The sensor of claim 2 wherein said single reflective surface is oriented at an angle of between 25 and 35 degrees with respect to the longitudinal fibre axes of said first and second optical fibres.

7. The sensor of claim 1 wherein said terminal ends of said first and second optical fibres are normal with respect to the longitudinal fibre axes of said first and second optical fibres.

8. The sensor of claim 1 wherein at least one of said single reflective surface and said terminal ends of said first and second optical fibres is shaped so as to focus the light reflected into the flow and to focus the field of view of the other of said first and second optical fibres.

9. The sensor of claim 1 wherein said first and second optical fibres each comprises a core and a surrounding cladding layer and wherein said optical cement has an index of refraction that is greater than an index of refraction of said cores.

10. The sensor of claim 1 wherein said first and second optical fibres each comprises a core and a surrounding cladding layer and wherein said optical cement has an index of refraction that is less than an index of refraction of said cores.

11. The sensor of claim 9 wherein said terminal ends of said first and second optical fibres are concave in shape.

12. The sensor of claim 10 wherein said terminal ends of said first and second optical fibres are convex in shape.

13. The sensor of claim 3 wherein said terminal ends of said first and second optical fibres are normal with respect to the fibre axes of said first and second optical fibres.

14. The sensor of claim 11 wherein said single reflective surface is concave.

15. The sensor of claim 12 wherein said single reflective surface is concave.

16. The sensor of claim 1 wherein at least one of said first and second optical fibres is a multimode optical fibre.

17. The sensor of claim 1 wherein at least one of said first and second optical fibres is a single mode optical fibre.

18. A sensor for remote fluid flow measurements, said sensor comprising:
    a flexible tube having at least one optical opening formed in a sidewall thereof;
    transmitting and receiving optical fibres disposed within said tube, said transmitting and receiving optical fibres each having a terminal end disposed within said tube proximate an associated opening of said at least one optical opening;
    at least one reflective surface disposed within said tube adjacent said terminal ends of said transmitting and receiving optical fibres, a transmitting reflective surface of said at least one reflective surface being associated with said transmitting optical fibre and a receiving reflective surface of said at least one reflective surface being associated with said receiving optical fibre; and
    said at least one reflective surface being oriented such that light emitted from said terminal end of said transmitting optical fibre is reflected by said transmitting reflective surface out said optical opening associated with said transmitting optical fibre into said fluid and so that back scattered light within a field of view of said receiving optical fibre reenters said optical opening associated with said receiving optical fibre to be reflected by said receiving reflective surface directly into said terminal end of said receiving optical fibre, said transmitting reflective surface and said receiving reflective surface being formed so that said emitted light and said field of view, respectively, are focused.

19. The sensor of claim 18 wherein said reflective surface associated with said transmitting optical fibre and said reflective surface associated with said receiving optical fibre comprise a common reflective surface.

20. The sensor of claim 18 wherein said optical opening associated with said transmitting optical fibre and said optical opening associated with said receiving optical fibre comprise a common optical opening.

21. The sensor of claim 19 wherein said optical opening associated with said transmitting optical fibre and said optical opening associated with said receiving optical fibre comprise a common optical opening.

22. The sensor of claim 18 wherein at least a one of said at least one reflective surface and said terminal ends of said transmitting and receiving optical fibres are shaped so as to focus the emitted light and said field of view.

23. The sensor of claim 18 wherein said at least one optical opening and a portion of said tube surrounding said terminal ends of said transmitting and receiving optical fibres and said at least one reflective surface define a cavity, said cavity being filled with an optical cement forming at least one optical window.

24. The sensor of claim 23 wherein said transmitting and receiving optical fibres each comprises a core and a surrounding cladding layer and wherein said optical cement has an index of refraction that is greater than an index of refraction of said cores.

25. The sensor of claim 23 wherein said transmitting and receiving optical fibres each comprises a core and a surrounding cladding layer and wherein said optical cement has an index of refraction that is less than an index of refraction of said cores.

26. The sensor of claim 24 wherein said terminal ends of said transmitting and receiving optical fibres are concave in shape.

27. The sensor of claim 25 wherein said terminal ends of said transmitting and receiving optical fibres are convex in shape.

28. The sensor of claim 18 wherein at least one of said transmitting and receiving optical fibres is a multimode optical fibre.

29. The sensor of claim 18 wherein at least one of said transmitting and receiving optical fibres is a single mode optical fibre.

30. The sensor of claim 18 wherein said at least one reflective surface is flat.

31. The sensor of claim 30 wherein said at least one reflective surface is oriented at an angle of between 25 and 35 degrees with respect to longitudinal axes of said transmitting and receiving optical fibres.

32. The sensor of claim 18 wherein said at least one reflective surface is disposed adjacent the distal end of said tube.

33. The sensor of claim 18 wherein said at least one reflective surface is composed of stainless steel.

34. The sensor of claim 18 wherein said at least one reflective surface is concave.

35. The sensor of claim 26 wherein said at least one reflective surface is concave.

36. The sensor of claim 27 wherein said at least one reflective surface is concave.

37. The sensor of claim 34 wherein said terminal ends of said transmitting and receiving optical fibres are normal with respect to longitudinal fibre axes of said transmitting and receiving optical fibres.

38. A method for making remote fluid flow measurements, said method comprising the steps of:
   transmitting an incident light beam through a first optical fibre, said first optical fibre disposed within a flexible tube;
   reflecting the incident light beam emitted from a terminal end of the first optical fibre off a first reflective surface, disposed in said flexible tube proximate said terminal end of said first optical fibre, out of an optical opening formed in a sidewall of the tube into a measurement volume of the flow located outside and alongside the tube, the reflected light beam being scattered within the measurement volume;
   receiving, from a second reflective surface, disposed in said flexible tube proximate said terminal end of said second optical fibre through a terminal end of a second optical fibre disposed within the tube, a portion of the scattered light beam that is within a field of view of the second optical fibre;
   focusing the incident light beam to increase intensity of the light beam reflected into the flow; and
   focusing the field of view of the second optical fibre.

39. The method of claim 38 wherein said incident light beam focusing step and said field of view focusing step include shaping the terminal ends of the first and second optical fibres.

40. The method of claim 38 wherein said incident light beam focusing step and said field of view focusing step include shaping the first and second reflective surfaces.

41. The method of claim 40 wherein said incident light beam focusing step and said field of view focusing step include shaping the first and second reflective surfaces so as to be concave.

42. A sensor for remote fluid flow measurements, said sensor comprising:
   a flexible tube having at least one optical opening formed in a sidewall thereof;
   transmitting and receiving optical fibres disposed within said tube, said transmitting and receiving optical fibres each having a terminal end disposed within said tube proximate an associated opening of said at least one optical opening;
   at least one reflective surface disposed within said tube adjacent said terminal ends of said transmitting and receiving optical fibres, a transmitting reflective surface of said at least one reflective surface being associated with said transmitting optical fibre and a receiving reflective surface of said at least one reflective surface being associated with said receiving optical fibre;
   said at least one reflective surface being oriented such that light emitted from said terminal end of said transmitting optical fibre is reflected by said transmitting reflective surface out said optical opening associated with said transmitting optical fibre into said fluid and so that back scattered light within a field of view of said receiving optical fibre reenters said optical opening associated with said receiving optical fibre to be reflected by said receiving reflective surface directly into said terminal end of said receiving optical fibre, said transmitting reflective surface and said receiving reflective surface being formed so that said emitted light and said field of view, respectively, are focused; and wherein said at least one optical opening and a portion of said tube surrounding said terminal ends of said transmitting and receiving optical fibres and said at least one reflective surface define a cavity, said cavity being filled with an optical cement forming at least one optical window.

43. The sensor of claim 42, wherein said reflective surface associated with said transmitting optical fibre and said reflective surface associated with said receiving optical fibre comprise a common reflective surface.

44. The sensor of claim 42 wherein said optical opening associated with said transmitting optical fibre and said optical opening associated with said receiving optical fibre comprise a common optical opening.

45. The sensor of claim 43 wherein said optical opening associated with said transmitting optical fibre and said optical opening associated with said receiving optical fibre comprise a common optical opening.

46. The sensor of claim 42 wherein at least a one of said at least one reflective surface and said terminal ends of said transmitting and receiving optical fibres are shaped so as to focus the emitted light and said field of view.

47. The sensor of claim 42, wherein said at least one optical opening and a portion of said tube surrounding said terminal ends of said transmitting and receiving optical fibres and said at least one reflective surface define a cavity, said cavity being filled with an optical cement forming at least one optical window.

48. The sensor of claim 47 wherein said transmitting and receiving optical fibres each comprises a core and a surrounding cladding layer and wherein said optical cement has an index of refraction that is greater than an index of refraction of said cores.

49. The sensor of claim 47 wherein said transmitting and receiving optical fibres each comprises a core and a surrounding cladding layer and wherein said optical cement has an index of refraction that is less than an index of refraction of said cores.

50. The sensor of claim 48 wherein said terminal ends of said transmitting and receiving optical fibres are concave in shape.

51. The sensor of claim 49 wherein said terminal ends of said transmitting and receiving optical fibres are convex in shape.

52. The sensor of claim 42 wherein at least one of said transmitting and receiving optical fibres is a multimode optical fibre.

53. The sensor of claim 42 wherein at least one of said transmitting and receiving optical fibres is a single mode optical fibre.

54. The sensor of claim 42 wherein said at least one reflective surface is flat.

55. The sensor of claim 54 wherein said at least one reflective surface is oriented at an angle of between 25 and 35 degrees with respect to longitudinal axes of said transmitting and receiving optical fibres.

56. The sensor of claim 42 wherein said at least one reflective surface is disposed adjacent the distal end of said tube.

57. The sensor of claim 42 wherein said at least one reflective surface is composed of stainless steel.

58. The sensor of claim 42 wherein said at least one reflective surface is concave.

59. The sensor of claim 50 wherein said at least one reflective surface is concave.

60. The sensor of claim 51 wherein said at least one reflective surface is concave.

61. The sensor of claim 58 wherein said terminal ends of said transmitting and receiving optical fibres are normal with respect to longitudinal fibre axes of said transmitting and receiving optical fibres.

* * * * *